United States Patent [19]

Krebs

[11] Patent Number: 4,539,154

[45] Date of Patent: Sep. 3, 1985

[54] POLYENE COMPOUNDS

[75] Inventor: Ernst P. Krebs, Bottmingen, Switzerland

[73] Assignee: Hoffmann-La Roche Inc., Nutley, N.J.

[21] Appl. No.: 504,554

[22] Filed: Jun. 15, 1983

[51] Int. Cl.³ .............................................. C11C 3/02
[52] U.S. Cl. ............................................. 260/410.9 N
[58] Field of Search ................... 260/404, 408, 413 K, 260/404.5, 410.9 R

[56] References Cited

U.S. PATENT DOCUMENTS

| | | | |
|---|---|---|---|
| 4,051,174 | 9/1977 | Stoller et al. | 260/413 L |
| 4,105,681 | 8/1978 | Bollag | 260/404 |
| 4,129,662 | 12/1978 | Gander et al. | 260/404 |
| 4,137,246 | 1/1979 | Chan et al. . | |
| 4,169,103 | 9/1979 | Haenni et al. | 260/413 L |
| 4,193,931 | 3/1980 | Loeliger | 424/308 |
| 4,225,527 | 9/1980 | Bollag et al. . | |

FOREIGN PATENT DOCUMENTS

| | | |
|---|---|---|
| 2456959 | 6/1976 | Fed. Rep. of Germany . |
| 2843884 | 4/1980 | Fed. Rep. of Germany . |
| 2081478 | 8/1974 | France . |
| 1335867 | 10/1973 | United Kingdom . |

OTHER PUBLICATIONS

Lewin et al., Chem. Abstracts, 96 181457e, (1982).
Lewin et al., J. Am. Chem. Soc., 103, 6527–6529, (1981).

Primary Examiner—Helen M. S. Sneed
Attorney, Agent, or Firm—Jon S. Saxe; Bernard S. Leon; William H. Epstein

[57] ABSTRACT

9-(cyclohexenyl or phenyl)-4,7-dimethyl-2,4,6,8-nonatetraenoic acid derivatives as well as 7-(5,6,7,8-tetrahydro-5,5,8,8,-tetramethyl-2-naphthyl)-4-methyl-2,4,6-octatrienoic acid derivatives useful for the treatment of neoplasms, premalignant lesions, acne, psoriasis and rheumatic diseases of an inflammatory or degenerative kind.

19 Claims, No Drawings

POLYENE COMPOUNDS

SUMMARY OF INVENTION

The present invention is concerned with novel polyene compounds, a process for their manufacture and pharmaceutical preparations which contain these polyene compounds.

The polyene compounds provided by the present invention are compounds of the formula

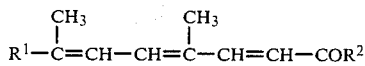
I wherein
$R^1$ is a group of the formula:

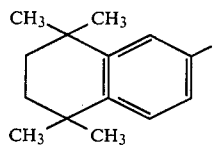 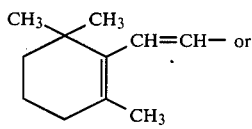

(a)        (b)

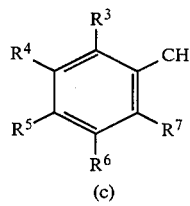

(c)

$R^2$ is hydroxy, lower-alkoxy, amino, mono-(lower-alkyl)amino or di(lower-alkyl)-amino, $R^3$ is lower-alkyl or halogen; $R^4$ is lower-alkyl; $R^5$ is lower-alkoxy; $R^6$ is hydrogen or lower-alkyl; and $R^7$ is lower-alkyl or halogen
and pharmaceutically acceptable salts of the carboxylic acids of formula I. These compounds and their salts are useful for treatment of neoplasms, premalignant lesions, acne, psoriasis and rheumatic diseases of an inflammatory or degenerative kind.

DETAILED DESCRIPTION

Among the compounds of formula I is a compound of the formula:

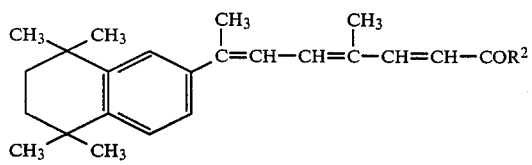
I-A wherein $R^2$ is as above.
In accordance with this invention, $R^2$ can be hydroxy, lower alkoxy amino, mono(lower alkyl)amino or di(-lower alkyl)amino, preferably hydroxy, lower alkoxy or mono(lower alkyl)amino.

Another compound of formula I is a compound of the formula:

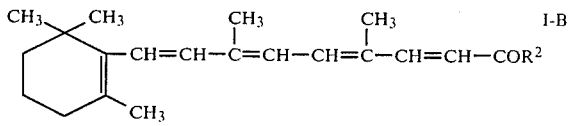
I-B wherein $R^2$ is as above.
In the compound of formula I-B, $R^2$ is preferably hydroxy or lower alkoxy.

Among the compounds of formula I are compounds of the formula:

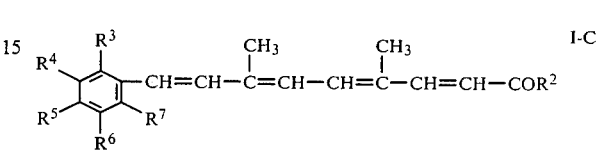
I-C wherein $R^2$, $R^3$, $R^4$, $R^5$, $R^6$ and $R^7$ are as above.

Preferred groups of formula I-C are those in which $R^3$, $R^4$ and $R^7$ are lower-alkyl, $R^5$ is lower-alkoxy and $R^6$ is hydrogen as well as those compounds where $R^2$ is hydroxy or lower alkoxy.

Alkyl groups and the alkyl moieties present in alkoxy and alkylamino groups preferably contain from 1 to 6 carbon atoms. They can be straight-chain or branched-chain alkyl groups such as, for example, the methyl, ethyl, isopropyl or 2-methylpropyl group, with methyl being especially preferred for $R^3$, $R^4$ and $R^7$ and methyl and ethyl being especially preferred for lower alkyl.

Methylamino and ethylamino are examples of preferred mono(alkyl)amino groups and diethylamino and dimethylamino is an example of a dialkylamino group. The compounds of formula I and the pharmaceutically acceptable salts of the carboxylic acids of formula I can be manufactured in accordance with the invention by reacting a compound of the general formula $R^1A$ with a compound of the general formula $$B-CH=\overset{CH_3}{\underset{|}{C}}-CH=CH-COR^2 \qquad II$$

wherein $R^1$ and $R^2$ have the significance given above and either A represents a 1-(triphenylphosphonium)-ethyl group of the formula

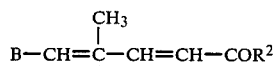

in which X represents phenyl and $Y^-$ represents the anion of an organic or inorganic acid, and B represents formyl; or A represents acetyl and B represents a dialkoxyphosphinylmethyl group of the formula

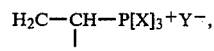

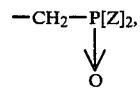

in which Z represents a lower-alkyl group; and, if desired, converting a carboxylic acid ester obtained into a carboxylic acid or acarboxylic acid amide, and also if desired, converting a carboxylic acid obtained into a pharmaceutically acceptable salt.

The chloride, bromide or hydrosulfate ion is the preferred inorganic acid anion denoted by Y and the tosyloxy ion is the preferred organic acid anion denoted by Y.

The reaction of a formyl compound of formula II with a phosphorane is carried out in a manner known per se in the presence of an acid-binding agent, for example in the presence of a strong base such as, for example, butyl lithium, sodium hydride or the sodium salt of dimethyl sulfoxide, if desired in a solvent, for example in an ether such as diethyl ether or tetrahydrofuran or in an aromatic hydrocarbon such as benzene, at a temperature between room temperature and the boiling point of the reaction mixture.

The reaction of a phosphonate of formula II with a compound of the formula $R^1COCH_3$ is also carried out in a manner known per se in the presence of a base and, preferably, in the presence of an inert organic solvent, for example in the presence of sodium hydride in benzene, toluene, dimethylformamide, tetrahydrofuran, dioxan or 1,2-dimethoxyethane or in the presence of a sodium alcoholate in an alkanol (e.g. sodium methylate in methanol), at a temperature between 0° C. and the boiling point of the reaction mixture.

The reactions describd earlier can also be carried out in situ, i.e. without isolating the phosphonium salt or phosphonate in question.

A carboxylic acid ester of formula I can be hydrolyzed in a manner known per se, for example by treatment with alkalis, especially by treatment with aqueous-alcoholic sodium or potassium hydroxide solution at a temperature between room temperature and the boiling point of the reaction mixture, and the resulting carboxylic acid can be amidated either via an acid halide or, as described hereinafter, directly.

A carboxylic acid of formula I, i.e. the compound of formula I wherein $R^2$ is hydroxy can be converted in a manner known per se to the corresponding acid chloride for example by treatment with thionile chloride, preferably in pyridine, or with phosphorus trichloride in toluene. The acid chloride can be converted into an ester by reaction with an alcohol or into a corresponding amide by reaction with an amine.

A carboxylic acid ester can be converted directly into the corresponding amide, for example by treatment with lithium amide. The lithium amide is advantageously reacted at room temperature with the ester in question.

A carboxylic acid of formula I forms pharmaceutically acceptable salts with bases, especially with alkali metal hydroxides and preferably with sodium hydroxide or potassium hydroxide.

Formula I hereinbefore includes both the cis and trans forms as well as mixtures thereof.

The compounds of formula I can occur as cis/trans mixtures which, if desired and in a manner known per se, can be separated into the cis and trans components or isomerized to the all-trans compounds. the all-trans (all-E) compounds are preferred.

The compounds of formula I and pharmaceutically acceptable salts of the carboxylic acids of formula I are useful as medicaments. They can be used for the topical and systemic therapy of benign and malignant neoplasms and of premalignant lesions as well as for the systemic and topical prophylaxis of these conditions.

They are also suitable for the topical and systemic therapy of acne, psoriasis and other dermatoses accompanied with an intensified or pathologically altered cornification as well as of inflammatory and allergic dermatological conditions. Further, the compounds of formula I and physiologically acceptable salts of the carboxylic acids of formula I can also be used for the control of disorders of the mucous membranes associated with inflammatory or degenerative or metaplastic changes and for the oral treatment of rheumatic diseases, especially those of an inflammatory and degenerative kind which affect the joints, muscles, tendons and other parts of the locomotor system. Examples of such diseases are primary cronic polyarthritis, spondylarthritis ankylopoetica Bechterew and psoriatic arthritis.

The compounds of formula I and its salts are active in inhibiting the growth of tumors. The tumor-inhibiting activity of the compounds of formula I and their pharmaceutically acceptable salts can be seen from the results of the papilloma test carried out by the procedure in Europ. J. Cancer 10, 731–737 [1974]. In this test, a regression of tumors induced with dimethylbenzanthracene and croton oil has been observed. The diameters of the papillomae decreased in the course of 2 weeks by about 49% following the intraperitoneal administration of 50 mg of ethyl(all-E)-4-methyl-7-(5,6,7,8-tetrahydro-5,5,8,8-tetramethyl-2-naphthyl)-2,4,6-octatrienoate.

The compounds of formula I and pharmaceutically acceptable salts of the carboxylic acids of formula I can be used as medicaments, for example in the form of pharmaceutical preparations. The pharmaceutical preparations for sytemic administration can be manufactured, for example, by adding a compound of formula I or a pharmaceutically acceptable salt of a carboxylic acid of formula I as the active ingredient to non-toxic, inert, solid or liquid carriers which are customary per se in such preparations. The pharmaceutical preparations can be administered enterally or parenterally with the preferred means of administration being oral. For oral administration there are suitable, for example, pharmaceutical preparations in the form of tables, capsules, dragees, syrups, suspensions, and solutions. In addition to these oral means, the compounds can be administered in the form of suppositories. For parenteral administration, there are suitable pharmaceutical preparations in the form of infusion or injection solutions.

The dosages in which the compounds of formula I and the pharmaceutically acceptable salts of the carboxylic acids of formula I are administered can vary according to the type of use, the mode of use and the requirements of the patients.

The compounds of formula I and the pharmaceutically acceptable salts of the carboxylic acids of formula I can be administered orally in amounts of about 0.01 to about 5 mg daily to an adult (75 kg) in one or more dosages. A preferred administration form comprises capsules for oral administration containing about 0.1 mg to about 1.0 mg of active substance.

The pharmaceutical preparations can contain inert as well as pharmacodynamically active additives. Tablets or ganulates, for example, can contain a series of binding agents, filling materials, carrier substances or diluents. Liquid preparations can take the form, for example, of a sterile solution which is miscible with water. Capsules can contain, in addition to the active substance, a filling material or thickening agent. Furthermore, flavoring-improving additives, substances usually used as preserving, stabilizing, moisture-retaining and emulsifying agents as well as salts for varying the osmotic pressure, buffers and other additives can also be present.

The previously mentioned carrier substances and diluents can be organic or inorganic substances; for example, water, gelatine, lactose, starch, magnesium stearate, talc, gum arabic, polyalkylene glycols and the like. A prerequisite is that all adjuvants used in the manufacture of the pharmaceutical preparations are non-toxic.

For topical administration, the compounds of formula I and pharmaceutically acceptable salts of the carboxylic acids of formula I are conveniently used in the form of salves, tinctures, creams, solutions, lotions, sprays, suspension and the like. Salves, creams and solutions are preferred. These pharmaceutical preparations for topical administration can be manufactured by mixing a compound of formula I or a pharmaceutically acceptable salt of a carboxylic acid of formula I as the active ingredient with non-toxic, inert, solid or liquid carriers which are customary per se in such preparations and which are suitable for topical treatment.

For topical administration, there are conveniently used topical compositions containing about 0.01% to about 5.0% by weight, of the compound of formula I and its pharmaceutically acceptable salts based upon the weight of the composition. With respect to solutions, these solutions preferably contain from about 0.1% to 3% by weight, especially 0.2% to 0.1% by weight, of the compound of formula I and/or its pharmaceutically acceptable salt. With respect to salves and creams, these salves or creams preferably contain the compound of formula I or its salt in an amount of from about 0.05% by weight to 5% by weight based upon the total weight of the cream or salves with amounts of from 0.05% by weight to about 1% by weight being especially preferred.

If desired, an antioxidant (e.g. tocopherol, N-methyl-γ-tocopheramine, butylated hydroxyanisole or butylated hydroxytoluene) can be incorporated in the pharmaceutical preparations.

The following Examples illustrate the present invention:

EXAMPLE 1

23.4 g of [1-(5,6,7,8-tetrahydro-5,5,8,8-tetramethyl-2-naphthyl)ethyl]-triphenylphosphonium bromide in 150 ml of dry tetrahydrofuran were treated slowly at −15° C. while stirring with 26.25 ml of 1.6 molar butyl lithium (in hexane). After 30 minutes, there were added dropwise at the same temperature 6.72 g (40 mmol) of ethyl (all-E)-5-formyl-4-methyl-2,4-pentadienoate in 30 ml of tetrahydrofuran and the mixture was subsequently stirred at room temperature for a further 2 hours. After the addition of ethyl acetate, the organic phase was shaken with 0.1N hydrochloric acid, washed neutral with water, dried over magnesium sulphate and concentrated on a rotary evaporator. Two-fold crystallization of the residue from about 100 ml of ethanol gave 3.47 g (24%) of ethyl (all-E)-4-methyl-7-(5,6,7,8-tetrahydro-5,5,8,8-tetramethyl-2-naphthyl)-2,4,6-octatrienoate of melting point 87.5°–89° C. A further 1.6 g of pure product could be obtained from the mother liquors by chromatography.

The ethyl (all-E)-5-formyl-4-methyl-2,4-pentadienoate can be prepared as follows:

(a) 43.23 g of triethyl phosphonoacetate were added to 4.63 g of sodium hydride in 100 ml of dry tetrahydrofuran. 25.0 g (0.18 mol) of γ-acetoxy-tiglic aldehyde in 50 ml of tetrahydrofuran were subsequently added dropwise at 0°–5° C. The mixture was stirred at room temperature for 20 hours, diluted with 200 ml of ethyl acetate, washed with saturated sodium chloride solution and dried over magnesium sulphate. Concentration and distillation at 103° C./0.35 mmHg gave 28.6 g (76%) of ethyl 6-acetoxy-4-methyl-2,4-hexadienoate.

(b) 27.5 g of ethyl 6-acetoxy-4-methyl-2,4-hexadienoate, 20 g of sodium carbonate and 2 ml of triethanolamine were heated to reflux for 3 hours in 250 ml of ethanol. After the addition of ethyl acetate, the organic phase was washed with saturated sodium chloride solution, dried over magnesium sulphate and concentrated. Distillation at 110° C./0.4 mmHg gave 15.7 g (71%) of ethyl 6-hydroxy-4-methyl-2,4-hexadienoate.

(c) 11.7 g of ethyl 6-hydroxy-4-methyl-2,4-hexadienoate in 200 ml of dichloromethane were stirred at room temperature for 4 hours with 30 g of manganese (IV) oxide. The solution was filtered and concentrated and the residue was then recrystallized from hexane/cyclohexane. There were obtained 9.1 g (78%) of ethyl 5-formyl-4-methyl-2,4-pentadienoate of melting point 48°–49° C.

EXAMPLE 2

In a manner analogous to that described in Example 1, from 1-methyl-3-(2,6,6-trimethyl-1-cyclohexen-1-yl)allyl-triphenylphosphonium chloride and ethyl 5-formyl-4-methyl-2,4-pentadienoate there is obtained ethyl 4,7-dimethyl-9-(2,6,6-trimethyl-1-cyclohexen-1-yl)-2,4,6,8-nonatetraenoate of melting point 65°–66° C. (from methanol).

EXAMPLE 3

In a manner analogous to that described in Example 1, from 1-methyl-3-(2,3,6-trimethyl-4-methoxyphenyl)allyl-triphenylphosphonium chloride and ethyl 5-formyl-4-methyl-2,4-pentadienoate there is obtained ethyl (all-E)-9-(4-methoxy-2,3,6-trimethylphenyl)4,7-dimethyl-2,4,6,8-nonatetraenoate.

EXAMPLE 4

9 g of ethyl (all-E)-4-methyl-7-(5,6,7,8-tetrahydro-5,5,8,8-tetramethyl-2-naphthyl)-2,4,6-octatrienoate are dissolved in 200 ml of ethanol and the solution is treated with a solution of 8.2 g of potassium hydroxide in 20 ml of water. After stirring at room temperature for 18 hours, the mixture is poured into ice-water, acidified with 2N sulphuric acid and the precipitated acid is filtered off. After recrystallization from methanol, there are obtained 7.8 g of (all-E)-4-methyl-7-(5,6,7,8-tetrahydro-5,5,8,8-tetramethyl-2-naphthyl)-2,4,6-octatrienoic acid in the form of yellow crystals of melting point 232°–234° C.

EXAMPLE 5

4.5 g of (all-E)-4-methyl-7-(5,6,7,8-tetrahydro-5,5,8,8-tetramethyl-2-naphthyl)-2,4,6-octatrienoic acid are dissolved in 200 ml of tetrahydrofuran and the solution is treated with 2.6 g of 1,1'-carbonyldiimidazole. After stirring at room temperature for 3 hours, the mixture is cooled to 5°–10° C. and a stream of ethylamine is introduced during 1 hour. After removing the cooling bath, the mixture is stirred at room temperature overnight. The mixture is subsequently poured into ice-water, acidified with 6N sulphuric acid and extracted with ethyl acetate. The organic phase is washed with 2N sodium carbonate solution and with saturated sodium chloride solution, dried over sodium sulphate and evaporated. After a further purification of the crude product by chromatography on silica gel using methylene chloride/acetone (95:5) for the elution and recrystallization from toluene, there are obtained 1.6 g of N-ethyl 4-methyl-7-(5,6,7,8-tetrahydro-5,5,8,8-tetramethyl-2-naphthyl)-2,4,6-octatrienamide in the form of yellow crystals of melting point 150°–159° C.

EXAMPLE 6

By the procedure of Example 4, ethyl 4,7-dimethyl-9-(2,6,6-trimethyl-1-cyclohexen-1-yl)-2,4,6,8-nonatetraenoate is converted to 4,7-dimethyl-9-(2,6,6-trimethyl-1-cyclohexen-1-yl)-2,4,6,8-nonatetraenoic acid.

EXAMPLE 7

By the procedure of Example 4, ethyl (all E)-9-(4-methoxy-2,3,6-trimethylphenyl)-4,7-dimethyl-2,4,6,8-nonatetraenoate is converted to (all E)-9-(4-methoxy-2,3,6-trimethylphenyl)-4,7-dimethyl-2,4,6,8-nonatetraenoic acid.

EXAMPLE A

Capsules can contain the following ingredients:

| | |
|---|---|
| Ethyl (all-E)-4-methyl-7-(5,6,7,8-tetrahydro-5,5,8,8-tetramethyl-2-naphthyl)-2,4,6-octatrienoate | 0.1 mg |
| Wax mixture | 50.5 mg |
| Vegetable oil | 98.9 mg |
| Ethylenediaminetetraacetic acid trisodium salt | 0.5 mg |

I claim:

1. A composition of matter selected from the group consisting of compounds of the formula:

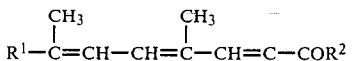

where
R₁ is selected from the group consisting of

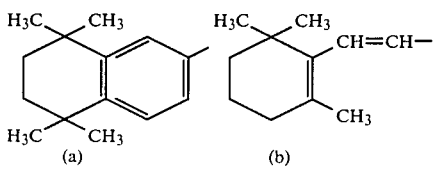

or

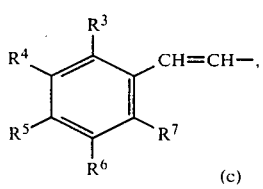

$R^2$ is hydroxy, lower alkoxy, amino, mono(lower alkyl)amino, or di(lower alkyl)amino; $R^3$ is lower alkyl or halogen, $R^4$ is lower alkyl; $R^5$ is lower alkoxy; $R^6$ is hydrogen or lower alkyl and $R^7$ is lower alkyl or halogen
and pharmaceutically acceptable salts thereof when $R^2$ is hydroxy.

2. The composition of claim 1 wherein $R^1$ is

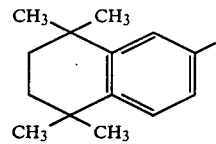

3. The composition of claim 2 wherein $R^2$ is hydroxy.
4. The composition of claim 3 wherein said compound is (all-E)-4-methyl-7-(5,6,7,8-tetrahydro-5,5,8,8-tetramethyl-2-naphthyl)-2,4,6-octatrienoic acid.
5. The composition of claim 2 wherein $R^2$ is lower alkoxy.
6. The composition of claim 5 wherein said compound is ethyl (all-E)-4-methyl-7-(5,6,7,8-tetrahydro-5,5,8,8tetramethyl-2-naphthyl)-2,4,6-octatrienoate.
7. The composition of claim 2 wherein $R^2$ is mono(-lower alkyl)amino.
8. The composition of claim 3 wherein said compound is N-ethyl 4-methyl-7-(5,6,7,8-tetrahydro-5,5,8,8-tetramethyl-2-naphthyl)-2,4,6-octatrienamide.
9. The compound of claim 1 wherein $R^1$ is

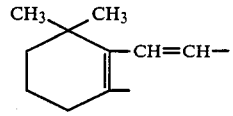

10. The composition of claim 9 wherein $R^2$ is hydroxy.
11. The composition of claim 10 wherein said compound is 4,7-dimethyl-9-(2,6,6-trimethyl-1-cyclohexen-1-yl)-2,4,6,8-nonatetraenoic acid.
12. The composition of claim 9 wherein $R^2$ is lower alkoxy.
13. The composition of claim 12 wherein said compound is ethyl 4,7-dimethyl-9-(2,6,6-trimethyl-1-cyclohexen-1-yl)-2,4,6,8-nonatetraenoate.
14. The composition of claim 1 wherein $R^1$ is

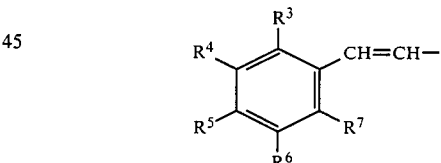

wherein $R^3$, $R^4$, $R^5$, $R^6$ and $R^7$ are as above.
15. The composition of claim 14 wherein $R^3$, $R^4$ and $R^7$ are lower alkyl, $R^5$ is lower alkoxy and $R^6$ is hydrogen.
16. The composition of claim 15 wherein $R^2$ is hydroxy.
17. The composition of claim 16 wherein said compound is (all-E)-9-(4-methoxy-2,3,6-trimethylphenyl)-4,7-dimethyl-2,4,6,8-nonatetraenoic acid.
18. The composition of claim 15 wherein $R^2$ is lower alkoxy.
19. The composition of claim 18 wherein said compound is ethyl (all-E)-9-(4-methoxy-2,3,6-trimethylphenyl)-4,7-dimethyl-2,4,6,8-nonatetraenoate.

* * * * *